(12) United States Patent
Li et al.

(10) Patent No.: US 11,547,071 B2
(45) Date of Patent: Jan. 10, 2023

(54) **METHODS FOR DISINFECTING AND INDUCING DIRECT RAPID PROLIFERATION OF EXPLANTS OF *KADSURA COCCINEA* STEMS WITH BUDS**

(71) Applicant: CENTRAL SOUTH UNIVERSITY OF FORESTRY AND TECHNOLOGY, Changsha (CN)

(72) Inventors: Ze Li, Changsha (CN); Yang Liu, Changsha (CN); Hui Zhang, Changsha (CN); Xiaoqin Zhang, Changsha (CN); Xiaohui Gao, Changsha (CN); Fangfang Ma, Changsha (CN); Jiayue Zhong, Changsha (CN); Xiaoyan Zhang, Changsha (CN); Sen Wang, Changsha (CN); Xiaofeng Tan, Changsha (CN); Ao Yang, Changsha (CN); Fen Bao, Changsha (CN); Ruonan Ma, Changsha (CN)

(73) Assignee: CENTRAL SOUTH UNIVERSITY OF FORESTRY AND TECHNOLOGY, Changsha (CN)

( * ) Notice: Subject to any disclaimer, the term of this patent is extended or adjusted under 35 U.S.C. 154(b) by 0 days.

(21) Appl. No.: 17/295,035

(22) PCT Filed: Jun. 4, 2020

(86) PCT No.: PCT/CN2020/094369
§ 371 (c)(1),
(2) Date: May 18, 2021

(87) PCT Pub. No.: WO2021/077755
PCT Pub. Date: Apr. 29, 2021

(65) Prior Publication Data
US 2022/0007606 A1    Jan. 13, 2022

(30) Foreign Application Priority Data
Oct. 23, 2019    (CN) .......................... 201911012181.9

(51) Int. Cl.
| | |
|---|---|
| *A01H 4/00* | (2006.01) |
| *A01G 2/10* | (2018.01) |
| *A01G 24/22* | (2018.01) |
| *A01G 7/06* | (2006.01) |
| *A01G 23/04* | (2006.01) |

(52) U.S. Cl.
CPC .............. *A01H 4/005* (2013.01); *A01G 2/10* (2018.02); *A01G 7/06* (2013.01); *A01G 23/04* (2013.01); *A01G 24/22* (2018.02); *A01H 4/00* (2013.01)

(58) Field of Classification Search
CPC ............ A01H 4/005; A01H 4/00; A01G 2/10; A01G 24/22; A01G 7/06; A01G 23/04
See application file for complete search history.

(56) References Cited

FOREIGN PATENT DOCUMENTS

| CN | 101228847 A | | 7/2008 |
| CN | 101878737 A | | 11/2010 |
| CN | 105393919 A | * | 3/2016 |
| CN | 105393919 A | | 3/2016 |
| CN | 110036912 A | | 7/2019 |
| CN | 110558233 A | | 12/2019 |

OTHER PUBLICATIONS

Cui et al. An efficient micropropagation protocol for an endangered ornamental tree species (Magnolia sirindhorniae Noot. & Chalermglin and assessment of genetic uniformity through DNA markers, Scientific Reports (2019) 9:9634, pp. 1-10. (Year: 2019).*
English translation CN105393919A, 2022 12 pp. (Year: 2022).*
Cui et al. An efficient micropropagation protocol for an endangered ornamental tree species (Magnolia sirindhorniae Noot. & Chalermglin) and assessment of genetic uniformity through DNA markers, Scientific Reports (2019) 9:9634, 1-10. (Year: 2019).*
Duhoky et al. Effect of different concentration of BA and IAA on micropropagation of Gardenia jasminoides, Mesopotamia J. of Agric ., vol. 38, No. 2, 2010, 14 pp. (Year: 2010).*
Gibson et al. Stock Plant Production and Management Basics for Small Greenhouse Businesses, University of Florida IFAS Extension ENH1021 (2005) 1-5. (Year: 2005).*
Jackson Nurseries, Plant Pot Size Guide, retrieved on Jul. 13, 2022 at https://www.jacksonsnurseries.co.uk/plant-pot-size-guide.html, 2 pp. (Year: 2022).*
Jedoroh et al. Induction of shoot and root from nodes of Kadsura heteroclita, International Journal of Agricultural Technology 2018 vol. 14(7): 1287-1292. (Year: 2018).*
Mitsukuri et al. Effects of Type of Explant and Dark Preconditioning of Bud Formation in Habenaria radiata (Thunb.) in Vitro, HortScience 44(2):523-525, 2009. (Year: 2009).*
CN105393919A English translation 2022, 12 pp. (Year: 2022).*
Wei Rongchang, et al., Cutting propagation method for kadsura coccinea, 2016, 3 pp. total.
Songping Hu, et al., Plant Cell and Tissue and Culture Technology, 2014, pp. 62, 3 pp. total.
Jiyuan Zhou, Plant cell engineering, 2007, pp. 41, 3 pp. total.

(Continued)

*Primary Examiner* — June Hwu
(74) *Attorney, Agent, or Firm* — Bayramoglu Law Offices LLC

(57) ABSTRACT

A method for disinfecting explants of *Kadsura coccinea* stems with buds and a method for directly inducing rapid proliferation of sterile buds by using the explants of *Kadsura coccinea* stems with buds involve processes such as selection, treatment and disinfection of explants, primary culture, subculture proliferation culture. The problem of difficulty in tissue culture and primary culture of *Kadsura coccinea* stems is solved, and the advantages include low contamination rate of explants, high propagation rate and robust proliferation of axillary buds. This allows obtaining sterile axillary buds of *Kadsura coccinea* through tissue culture, and provides support for tissue culture, rapid propagation and factory seedling of *Kadsura coccinea* in the future.

16 Claims, 3 Drawing Sheets

(56) References Cited

OTHER PUBLICATIONS

Wenbing Yao, Introduction to Biotechnology Pharmacy, 2015, pp. 125, 3 pp. total.
Jedoroh, N., et al., Induction of shoot and root from nodes of Kadsura Iteteroclita, International Journal of Agricultural Technology, 2018, pp. 1287-1292, vol. 14(7).

* cited by examiner

METHODS FOR DISINFECTING AND INDUCING DIRECT RAPID PROLIFERATION OF EXPLANTS OF KADSURA COCCINEA STEMS WITH BUDS

CROSS REFERENCE TO THE RELATED APPLICATIONS

This application is the national phase entry of International Application No. PCT/CN2020/094369, filed on Jun. 4, 2020, which is based upon and claims priority to Chinese Patent Application No. 201911012181.9, filed on Oct. 23, 2019, the entire contents of which are incorporated herein by reference.

TECHNICAL FIELD

The present invention belongs to the field of tissue culture of *Kadsura coccinea*, and specifically relates to a method for disinfecting explants of *Kadsura coccinea* stems with buds and a method for directly inducing rapid proliferation of sterile buds by using the explants of *Kadsura coccinea* stems with buds.

BACKGROUND

*Kadsura coccinea* is an evergreen liana, belonging to genus *Kadsura* from the Magnoliaceae family. Its fruit is big and unique aggregate fruit with a diameter of 10-12 cm and a weight of about 600 g looks like a football, the biggest fruit is 1200 g, a young fruit is blue-green, and a mature fruit is deep red. The flesh looks like a grape, with a lychee color and an apple aroma. With good color, aroma, and taste, *Kadsura coccinea* is a third-generation new fruit tree which has an edible value, a medicinal value, a greening value, an ornamental value, a high development potential and many functions and needs to be developed urgently. *Kadsura coccinea* grows in Vietnam and China and mainly grows in Jiangxi, Hunan, Guangdong, Hong Kong, Hainan, Guangxi, Sichuan, Guizhou, and Yunnan (Pingbian, Hekou, Jinping, Mengzi, Wenshan, Simao and Jingdong) of China. *Kadsura coccinea* grows in forests with an altitude of 1500-2000 m. It can be used for promoting Qi and blood circulation, reducing swelling and pain, treating stomach diseases, rheumatism and osteodynia and relieving traumatic injuries and blood stasis, and is commonly used in the gynecology department. *Kadsura coccinea* is high in adaptability, so it has no requirements for soil, and can vigorously grow with few pests and diseases, and adult trees can withstand a high temperature of 40° C. or above and a low temperature of −20° C. Therefore, *Kadsura coccinea* can be planted in mountains, hills, and plains.

However, at present, *Kadsura coccinea* is mainly propagated by sowing, and there is no vegetative propagation technology system for good varieties, so that popularization of good varieties and healthy development of the industry are limited. According to the present invention, the problem of long propagation cycle of seedlings can be solved by using stems with buds for rapid propagation of good varieties of *Kadsura coccinea*. Currently, researches on tissue culture of *Kadsura coccinea* plants are still in an initial stage. The main problems are that explants are very difficult to disinfect and likely to be contaminated and sterile seedlings cannot be obtained. Therefore, the production of virus-free seedlings by vegetative propagation of *Kadsura coccinea* is severely limited. In the aspects of tissue culture and vegetative propagation, by inducing axillary buds with *Kadsura coccinea* stems with buds, the following advantages are achieved that the culture cycle is short, the axillary buds are robust, and the proliferation coefficient is high, and thus factory seedling of *Kadsura coccinea* is facilitated.

According to the research of the effects of cutting season and stem treatment on the survival rate of *Kadsura coccinea* by Wei Rongchang et al. (2015), the results show that the cutting survival rate is the highest from May to July and low in other seasons, during which mass propagation of *Kadsura coccinea* is not facilitated. Tissue culture is an important approach for rapidly propagating virus-free seedlings of good varieties of plants and has a broad commercial prospect. According to the report on tissue culture of *Kadsura coccinea* by Wei Rongchang et al. (2015), young leaves of *Kadsura coccinea* are used to induce re-differentiation of callus tissues to obtain adventitious buds, the whole culture process is extremely complicated. It takes at least 87 days from inoculation to proliferation of buds, the culture cycle is extremely long, and there are no pictures showing growth conditions. However, according to the present invention, the operation is simple, the contamination rate is low, good growth of axillary buds is achieved, the culture cycle can be shortened to less than 30 days, the number of axillary buds after primary induction can be 8.0 or above (FIG. 8), and the problem of difficulty in inducing axillary buds through primary culture of *Kadsura coccinea* is significantly solved. Rooting culture and factory seedling of *Kadsura coccinea* in the later period are facilitated.

In conclusion, in a tissue culture process of *Kadsura coccinea* stems with buds, explants are likely to be contaminated during primary culture. According to the present invention, a large number of sterile buds of *Kadsura coccinea* are obtained efficiently in a short period of time mainly in a series of processes such as transplanting, disinfection, primary culture, and subculture proliferation of explants of *Kadsura coccinea* stems with buds, thus providing a possibility for factory seedling and of *Kadsura coccinea* and transformation of a genetic system.

SUMMARY

A main objective of the present invention is to provide a method for disinfecting explants of *Kadsura coccinea* stems with buds in order to solve the problems that currently explants of *Kadsura coccinea* stems with buds are difficult to sterilize and likely to have endophytic bacteria. The disinfection method is simple and efficient and has a good sterilization effect, laying a solid foundation for tissue culture and rapid propagation of *Kadsura coccinea*.

A method for disinfecting explants of *Kadsura coccinea* stems with buds sequentially includes the following steps:

(1) obtaining materials: transplanting *Kadsura coccinea* cultivated in a field indoors, cutting off stems and leaves of overground parts, and using germinated semi-lignified stems with buds as explant materials after 3-5 months;

(2) treating the explants: cutting the semi-lignified stems with buds into 3-4 cm long stems, each containing one axillary bud, washing the stems with a detergent 1-2 times, and then rinsing the stems with running water for at least 1 hour; and (3) disinfecting the explants: soaking the semi-lignified *Kadsura coccinea* stems with buds after rinsing with running water in 75% alcohol for 1 minute and in another 75% alcohol for 1 minute, rinsing the stems with sterile water 3-4 times, disinfecting the stems with 0.1% mercuric chloride for 45 minutes, and finally rinsing the stems with sterile water 5-6 times, where mercuric chloride is changed every 15 minutes, 3 times in total.

Further, step (1) specifically includes transplanting biennial to triennial *Kadsura coccinea* cultivated in a field into pots indoors from January to April, cutting off stems and leaves of the overground parts, and using germinated semi-lignified stems with buds as test materials after 3-5 months.

Further, the pots in step (1) are 25-30 cm in height and 20-25 cm in diameter.

According to the present invention, it is found through a large number of experiments in the early stage that it is very difficult to directly disinfect explants of *Kadsura coccinea* stems with buds, and various disinfection and sterilization methods are used without success. However, it is accidentally found that when *Kadsura coccinea* cultivated in a field is transplanted indoors, stems and leaves of the overground parts are cut off and germinated semi-lignified stems with buds as explant materials after 3-5 months are subjected to disinfection, the effect is significant.

A second objective of the present invention is to provide a method for directly inducing rapid proliferation of sterile buds by using explants of *Kadsura coccinea* stems with buds. By adopting the method, explants of stems with buds are sterilized to directly induce axillary buds, the induction rate is high, the proliferation effect is good, the primary induction and proliferation coefficient can reach 8 or above, improving the possibility in factory seedling and genetic transformation in the future.

A method for directly inducing rapid proliferation of sterile buds by using explants of *Kadsura coccinea* stems with buds includes the following steps:

1) inducing axillary buds (namely primary induction): inoculating each disinfected stem with an axillary bud into a culture medium ½ MS+2.0-3.0 mg/L 6-BA+0.2 mg/L IAA to induce axillary buds, culturing the stems in dark for 2 days, and then transferring the stems to culture under light conditions; and 2) performing subculture proliferation: cutting and inoculating the robust axillary buds obtained after stem differentiation into a culture medium ½ MS+2.0-3.0 mg/L 6-BA+0.1-0.5 mg/L IBA for proliferation culture of the axillary buds.

Further, during induction of the axillary buds, the stems are cultured in dark for 2 days and then transferred to culture under light conditions for 30-35 days. The subculture proliferation culture is performed under light conditions for 30-35 days.

Further, the culture temperature is 26±1° C., the light culture intensity is 2100-2200 lx, and the light culture time 12-14 h/d.

Further, the culture medium for inducing the axillary buds is preferably: ½ MS+2.0 mg/L 6-BA+0.2 mg/L IAA.

Further, the culture medium for subculture proliferation culture is preferably: ½ MS+3.0 mg/L 6-BA+0.1-0.5 mg/L IBA.

Further, the culture media used in the method are each additionally provided with 30 g/L sucrose and 7 g/L agar, and the pH is adjusted to 5.5-5.8.

Preferably, each disinfected stem with an axillary bud is disinfected by using the method of the present invention.

The present invention mainly aims at the problems that sterile axillary buds of tissue culture seedlings of *Kadsura coccinea* cultivated in a field cannot be obtained and are all contaminated (FIG. 1) even if the sterile axillary buds are disinfected with 75% alcohol for 3 minutes and 0.1% mercuric chloride for 45 minutes; if the disinfection time becomes longer, although contamination can be controlled, tissues of all stems are killed and blackened, and axillary buds cannot grow (FIG. 2); a large number of tests show that sterile axillary buds are very difficult to obtain with field materials (Table 1); although some stems are not contaminated in the early stage, fungal contamination occurs when the axillary buds grow up a month later (FIG. 3); and not less than 50 bottles are used in each test, and a total of not less than 1000 bottles are used in a total of 20 tests. Therefore, according to the present invention, biennial to triennial *Kadsura coccinea* seedlings in a field are transplanted into flowerpots, with overground parts cut off, and then brought indoors for culture, and semi-lignified stems of the potted seedlings are used as explants. Through explorations in pretreatment, disinfection, primary culture, subculture proliferation culture and other aspects of the explants, it is found that the contamination rate during primary culture is significantly reduced when *Kadsura coccinea* seedlings are transplanted into the flowerpots for culture indoors, the technical problem of difficulty in primary culture is solved, sterile buds of *Kadsura coccinea* stems with buds are successfully obtained through tissue culture, the contamination problem during primary culture is basically controlled, and a reference is provided for solving the problem of easy contamination during primary culture of *Kadsura coccinea*. In addition, according to the present invention, the sterile buds are directly induced by stems with buds rather than callus tissues, the time for obtaining the sterile buds is significantly shortened, and the obtained sterile buds have high proliferation coefficient and good quality, so that a rapid propagation technology system suitable for the early stage of tissue culture of sterile buds of *Kadsura coccinea* test-tube seedlings is formed, and a foundation is laid for factory seedling and subsequent genetic engineering improvement of *Kadsura coccinea*.

DETAILED DESCRIPTION OF THE EMBODIMENTS

Figure 1:
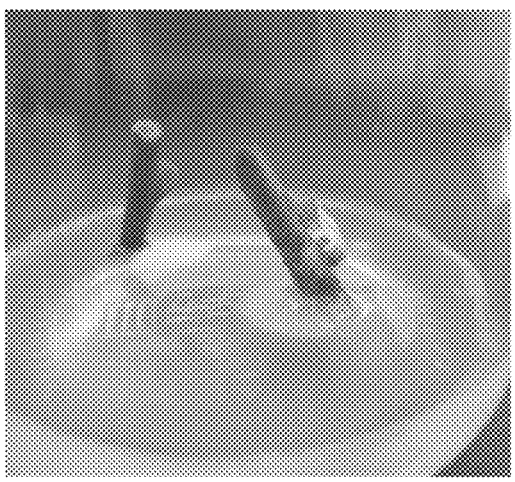
FIG. 1 is a photograph showing contamination of a stem with a bud of *Kadsura coccinea* cultivated in a field in an early stage of inoculation according to the present invention.
Figure 2:
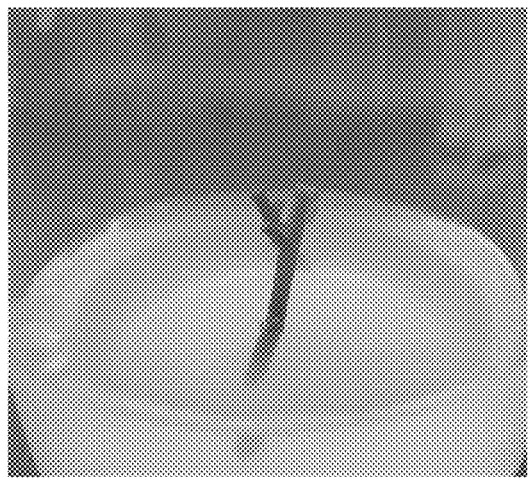
FIG. 2 is a photograph showing browning of a stem with a bud of *Kadsura coccinea* cultivated in a field when the disinfection time is long according to the present invention.
Figure 3:
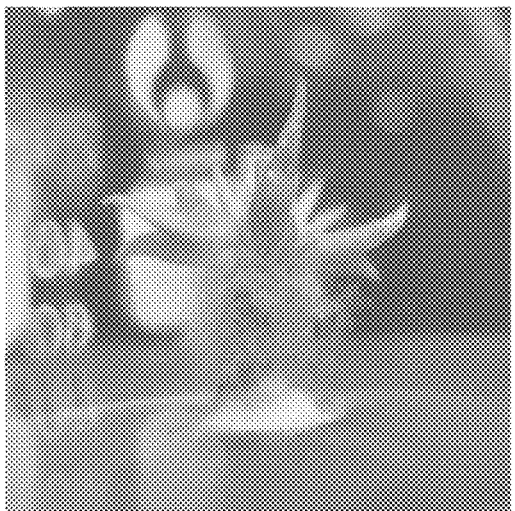
FIG. 3 is a photograph showing contamination of a stem with a bud of *Kadsura coccinea* cultivated in a field when culture is performed for 1 month according to the present invention.
Figure 4:
FIG. 4 is a photograph showing germinated new shoots when seedlings of *Kadsura coccinea* cultivated in a field are transplanted into a laboratory pot according to the present invention.

The following embodiment is used to further illustrate the present invention, but not to limit the present invention.

Embodiment 1

Following operations are performed in sequence:

1. Transplanting of field materials: Biennial to triennial *Kadsura coccinea* cultivated in a field were transplanted into plastic pots with a height of 30 cm and a diameter of 25 cm from January to April each year, with stems and leaves of the overgrounds cut off, watered and brought into a greenhouse on the roof of a laboratory of a tree building of Central South University of Forestry and Technology for normal water and fertilizer management for 3-5 months, and germinated semi-lignified stems with buds were used as test materials in the present invention.

2. Treatment of explants: The semi-lignified stems with buds were cut into 3-4 cm long stems, each containing one axillary bud, and the stems were washed with a detergent 1-2 times in a breaker and then rinsed with running water for at least 1 hour to rinse out mucus secreted by the stems for use.

3. Disinfection treatment of the explants: The semi-lignified *Kadsura coccinea* stems were selected in a sunny morning from July to October in 2018 to 2019 and brought to the laboratory, after the leaves were removed, the collected stems were rinsed with running water 1-2 times, rinsed with an appropriate amount of a detergent solution 1-2 times, repeatedly rinsed with running water for 60 minutes to rinse out the mucus secreted by the stems, placed on an ultra-clean workbench and disinfected with 75% alcohol, a 0.1% mercuric chloride solution and a 5% sodium hypochlorite solution. Different time gradients were set, the materials collected directly from the field were shown in Table 1, and the materials collected on the roof were shown in Table 2. The stems were stirred constantly with tweezers during disinfection and rinsed with sterile water 5-6 times, water on surfaces of the stems is absorbed with sterile filter paper, browned parts at both ends are cut off with a sterile knife, each stem with one bud was inoculated into a culture medium, and the contamination rate and the browning rate are counted.

TABLE 1

Disinfection effects of different disinfection treatment on stems of *Kadsura coccinea* cultivated in field

| Number | 75% alcohol(s) | 5% sodium hypochlorite (min) | 0.1% mercuric chloride (min) | Contamination rate (%) | Browning rate (%) | Induced survival rate of axillary buds (%) |
|---|---|---|---|---|---|---|
| $A_1$ | 1.5 | 0 | 30 | 100 | 0 | 0 |
| $A_2$ | 1.5 | 0 | 35 | 90.47 | 9.5 | 0 |
| $A_3$ | 1.5 | 0 | 40 | 82.61 | 17.19 | 0 |
| $A_4$ | 2 | 0 | 35 | 88.24 | 11.76 | 0 |
| $A_5$ | 2 | 0 | 40 | 74.07 | 25.93 | 0 |
| $A_6$ | 2 | 0 | 45 | 63.98 | 36.02 | 0 |
| $A_7$ | 2 | 0 | 50 | 45.62 | 54.38 | 0 |
| $A_8$ | 9 | 23 | 0 | 100 | 0 | 0 |
| $A_9$ | 2 | 25 | 0 | 100 | 0 | 0 |
| $A_{10}$ | 3 | 0 | 35 | 53.85 | 46.15 | 0 |
| $A_{11}$ | 3 | 0 | 40 | 43.52 | 56.58 | 0 |

TABLE 2

Disinfection effects of different disinfection treatment on potted *Kadsura coccinea* stems

| Number | 75% alcohol(s) | 5% sodium hypochlorite (mm) | 0.1% mercuric chloride (min) | Contamination rate (%) | Browning rate (%) | Induction rate of axillary buds (%) |
|---|---|---|---|---|---|---|
| $A_1$ | 1.5 | 0 | 30 | 100 | 0 | 0 |
| $A_2$ | 1.5 | 0 | 35 | 65.4 | 16.6 | 18.0 |
| $A_3$ | 1.5 | 0 | 40 | 53.1 | 14.3 | 32.6 |
| $A_4$ | 2 | 0 | 30 | 72.6 | 7.2 | 20.2 |
| $A_5$ | 2 | 0 | 35 | 58.2 | 16.8 | 25.0 |
| $A_6$ | 2 | 0 | 40 | 43.0 | 20.4 | 36.6 |
| $A_7$ | 2 | 0 | 45 | 18.5 | 21.7 | 59.8 |
| $A_8$ | 2 | 0 | 50 | 10.5 | 33.7 | 55.8 |
| $A_9$ | 2 | 25 | 0 | 84.1 | 15.9 | 0 |
| $A_{10}$ | 3 | 0 | 40 | 38.6 | 28.3 | 33.1 |
| $A_{11}$ | 3 | 0 | 45 | 15.1 | 30.5 | 54.4 |

It is finally confirmed that a preferred disinfection method of the present invention includes the following steps:

(1) obtaining materials; transplanting *Kadsura coccinea* cultivated in a field indoors, and using germinated semi-lignified stems with buds as test materials;

(2) treating explants, cutting the semi-lignified stems with buds into 3-4 cm long stems, each containing one axillary bud, washing the stems with a detergent 2 times, and then rinsing the stems with running water for 1 hour; and (3) disinfecting the explants: soaking the semi-lignified *Kadsura coccinea* stems with buds after rinsing with running water in 75% alcohol for 1 minute and in another 75% alcohol for 1 minute, rinsing the stems with sterile water 4 times, disinfecting the stems with 0.1% mercuric chloride for 45 minutes, and finally rinsing the stems with sterile water 5-6 times, where mercuric chloride is changed every 15 minutes, 3 times in total.

Figure 5:
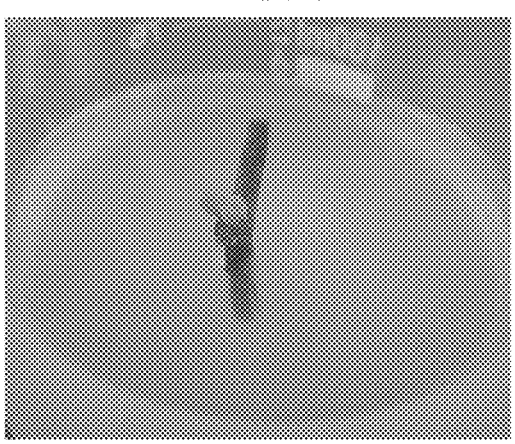
FIG. 5 is a photograph showing potted seedlings of *Kadsura coccinea* when primary culture is performed for 10 days according to the present invention.
Figure 6:
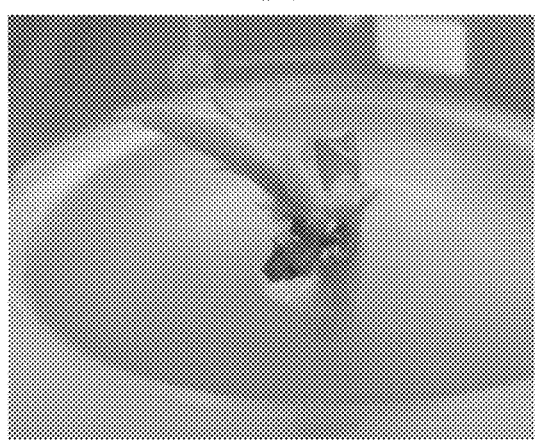
FIG. 6 and FIG. 7 are photographs showing potted seedlings of *Kadsura coccinea* when primary culture is performed for 20 days according to the present invention.
Figure 7:
Figure 8:
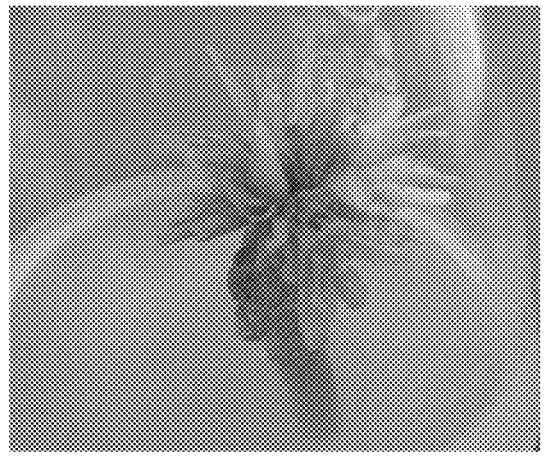
FIG. 8 and FIG. 9 are photographs showing potted seedlings of *Kadsura coccinea* when primary culture is performed for 30 days according to the present invention.
Figure 9:

The disinfected explants are inoculated into a ½MS culture medium according to a hormone formula in Table 3 for induction of axillary buds, cultured in dark for 2 days and then cultured under light conditions for 30-35 days, and the highest induction rate can reach 46.15%. 30 g/L sucrose and 7 g/L agar are additionally provided, and the pH is 5.5-5.8. The culture temperature is 26±1° C., the light intensity is 2100-2200 lx, and the light time is 12-14 h/d; (see FIG. 5), and the proliferation coefficient after primary culture can reach 8 or above.

TABLE 3

Effects of different plant growth regulators on primary culture of *Kadsura coccinea* stems

| Number | 6-BA concentration/ mg/L | IAA concentration/ mg/L | $GA_3$ concentration/ mg/L | Induction rate of axillary buds/% | Number of axillary buds (pieces) | Growth conditions |
|---|---|---|---|---|---|---|
| $B_1$ | 0 | 0 | 0 | 0 | 0 | No axillary buds grow |
| $B_2$ | 0 | 0.1 | 0 | 5.53 | 1.0 | Axillary buds are weak, thin and yellow |
| $B_3$ | 0 | 0.5 | 0 | 10.67 | 1.0 | Axillary buds are slender and yellow |
| $B_4$ | 1.0 | 0.1 | 0 | 35.39 | 5.0 | Axillary buds are short, and callus tissues grow in stem base parts at the upper end of the culture medium |
| $B_5$ | 1.0 | 1.0 | 0 | 31.07 | 3.0 | Axillary buds are tender and slender |
| $B_6$ | 2.0 | 0.2 | 0 | 46.15 | 8.2 | Axillary buds are robust and grow well with many cluster buds |
| $B_7$ | 2.0 | 0.5 | 0 | 37.5 | 7.0 | Callus tissues grow in stem base parts, and axillary buds are green |
| $B_8$ | 2.0 | 1.0 | 0 | 32.14 | 6.0 | Axillary buds are short, and leaves are small and a little curly with red front parts |
| $B_9$ | 3.0 | 0.2 | 0 | 53.12 | 7.6 | Stem base parts are big with a few of callus tissues, and many axillary buds grow |
| $B_{10}$ | 3.0 | 0.5 | 0 | 48.50 | 4.0 | Axillary buds are tight, and stem base parts are big and green |
| $B_{11}$ | 3.0 | 1.0 | 0 | 32.14 | 3.5 | A large number of callus tissues grow in stem base parts |
| $B_{12}$ | 0 | 0 | 1.0 | 10.35 | 1.0 | Axillary buds are short and brittle with red front parts |
| $B_{13}$ | 0 | 0 | 2.0 | 27.14 | 1.0 | Callus tissues grow in base parts, and buds grow poorly |

Figure 10:
FIG. 10, FIG. 11, and FIG. 12 are photographs showing potted seedlings of *Kadsura coccinea* when subculture proliferation culture is performed for 10 days according to the present invention.
Figure 11:
Figure 12:
Figure 13:
FIG. 13 is a photograph showing whole potted seedlings of *Kadsura coccinea* during primary culture according to the present invention.

The axillary buds are subjected to subculture proliferation culture. The axillary buds P obtained after primary culture are cut and inoculated into a ½MS culture medium according to a hormone formula in Table 4 for proliferation culture under light conditions for 30-35 days, and the highest proliferation coefficient is 8.5. 30 g/L sucrose and 7 g/L agar are additionally provided, and the pH is 5.5-5.8. The culture temperature is 26±1° C., the light intensity is 2100-2200 lx, and the light time is 12-14 h/d (see FIG. 10 to FIG. 12).

TABLE 4

Effects of different plant growth regulators on subculture proliferation culture of potted *Kadsura coccinea*

| Number | ZT concentration/ mg/L | IAA concentration/ mg/L | 2ip concentration/ mg/L | IBA concentration/ mg/L | 6-BA concentration/ mg/L | Proliferation coefficient |
|---|---|---|---|---|---|---|
| $C_1$ | 1 | 0.1 | 1 | 0 | 0 | 1.0 |
| $C_2$ | 2 | 0.1 | 1 | 0 | 0 | 2.0 |
| $C_3$ | 2 | 0.2 | 2 | 0 | 0 | 4.0 |
| $C_4$ | 0 | 0 | 0 | 0.1 | 1 | 3.2 |

What is claimed is:

1. A method for disinfecting an explant of a *Kadsura coccinea* stem with buds, sequentially comprising the following steps:
   (a) obtaining the explant: transplanting *Kadsura coccinea* plant cultivated in a field to indoors, cutting off stems and leaves of overground parts, and after 3-5 months using a germinated semi-lignified stem with buds as the explant after 3-5 months;
   (b) treating the explant by cutting the germinated semi-lignified stem with the buds into 3-4 cm long stems, wherein each of the 3-4 cm long stems is a semi-lignified *Kadsura coccinea* stem containing an axillary bud, washing the semi-lignified *Kadsura coccinea* stem with a detergent 1-2 times, and then rinsing the semi-lignified *Kadsura coccinea* stem with running water for at least 1 hour; and
   (c) disinfecting the explant by soaking the semi-lignified *Kadsura coccinea* stems after rinsing with running water in 75% alcohol for 1 minute and in another 75% alcohol for 1 minute, rinsing the semi-lignified *Kadsura coccinea* stem with sterile water 3-4 times, disinfecting the semi-lignified *Kadsura coccinea* stem with 0.1% mercuric chloride for 45 minutes, and finally rinsing the semi-lignified *Kadsura coccinea* stem with sterile water 5-6 times to obtain a disinfected explant of the *Kadsura coccinea* stem with the buds, wherein the 0.1% mercuric chloride is changed every 15 minutes, 3 times in total.

2. The method according to claim 1, wherein step (a) comprises transplanting biennial to triennial *Kadsura coccinea* plant cultivated in the field into pots indoors from January to April.

3. The method according to claim 2, wherein the pots in step (a) each have a height of 25-30 cm and a diameter of 20-25 cm.

4. A method for directly inducing rapid proliferation of buds in a disinfected explant of a *Kadsura coccinea* stem containing the buds, comprising:
   (a) obtaining an explant by transplanting *Kadsura coccinea* plant cultivated in a field to indoors, cutting off stems and leaves of overground parts, and after 3-5 months using a germinated semi-lignified stem with buds as the explant;
   (b) treating the explant by cutting the germinated semi-lignified stem with the buds into 3-4 cm long stems, wherein each of the 3-4 cm long stems is a semi-lignified *Kadsura coccinea* stem containing an axillary bud, washing the semi-lignified *Kadsura coccinea* stem with a detergent 1-2 times, and then rinsing the semi-lignified *Kadsura coccinea* stem with running water for at least 1 hour;
   (c) disinfecting the explant by soaking the semi-lignified *Kadsura coccinea* stem after rinsing with running water in 75% alcohol for 1 minute and in another 75% alcohol for 1 minute, rinsing the semi-lignified *Kadsura coccinea* stem with sterile water 3-4 times, disinfecting the semi-lignified *Kadsura coccinea* stem with 0.1% mercuric chloride for 45 minutes, and finally rinsing the semi-lignified *Kadsura coccinea* stem with sterile water 5-6 times to obtain the disinfected explant of the *Kadsura coccinea* stem containing the buds, wherein the 0.1% mercuric chloride is changed every 15 minutes, 3 times total;
   (d) inducing axillary buds by inoculating the disinfected explant of the *Kadsura coccinea* stem containing the buds into a first Murashige and Skoog ("MS") culture medium of ½ MS+2.0-3.0 mg/L 6-Benzylaminopurine ("6-BA")+0.2 mg/L Indole-3-acetic acid ("IAA") to induce the axillary buds, culturing the disinfected explant of the *Kadsura coccinea* stem in dark for 2 days, and then transferring the disinfected explant of the *Kadsura coccinea* stem to culture under light conditions; and
   (e) performing subculture proliferation by cutting and inoculating the axillary buds obtained after a stem differentiation in step (4) into a second IVIS culture medium of ½ MS+2.0-3.0 mg/L 6-BA+0.1-0.5 mg/L Indole-3-butyric acid("IBA") for proliferation culture of the axillary buds.

5. The method according to claim 4, wherein during step (d), the disinfected explant of the *Kadsura coccinea* stem is transferred to culture under the light conditions for 30-35 days.

6. The method according to claim 5, wherein for the light conditions, a culture temperature is 26±1° C., a light culture intensity is 2100-2200 lx, and a light culture time 12-14 h/d.

7. The method according to claim 4, wherein the first culture medium in step (d) for inducing the axillary bud is ½ MS+2.0 mg/L 6BA+0.2 mg/L IAA.

8. The method according to claim 4, wherein the second culture medium in step (e) for the subculture proliferation is ½ MS+3.0 mg/L 6BA+0.1-0.5 mg/L IBA.

9. The method according to claim 4, wherein the first culture medium in step (d) and the second culture medium in step (e) are each additionally provided with 30 g/L sucrose and 7 g/L agar, and a pH adjusted to 5.5-5.8.

10. The method according to claim 4, wherein step (a) comprises transplanting biennial to triennial *Kadsura coccinea* plant cultivated in the field into pots indoor from January to April.

11. The method according to claim 10, wherein the pots in step (a) each have a height of 25-30 cm and a diameter of 20-25 cm.

12. The method according to claim 5, wherein step (a) comprises transplanting biennial to triennial *Kadsura coccinea* plant cultivated in the field into pots indoors from January to April.

13. The method according to claim 12, wherein the pots in step (a) each have a height of 25-30 cm and a diameter of 20-25 cm.

14. The method according to claim 6, wherein step (a) comprises transplanting biennial to triennial *Kadsura coccinea* plant cultivated in the field into pots indoors from January to April.

15. The method according to claim 14, wherein the pots in step (a) each have a height of 25-30 cm and a diameter of 20-25 cm.

16. The method according to claim 7, wherein step (a) comprises transplanting biennial to triennial *Kadsura coccinea* plant cultivated in the field into pots indoors from January to April.

* * * * *